United States Patent
Nelson et al.

(10) Patent No.: US 10,064,835 B2
(45) Date of Patent: Sep. 4, 2018

(54) COMBINATION OF BETA-HYDROXY-BETA-METHYLBUTYRATE, ARGININE AND GLUTAMINE FOR USE IN TREATING DIABETIC ULCERS

(71) Applicant: ABBOTT LABORATORIES, Abbott Park, IL (US)

(72) Inventors: Jeffrey L. Nelson, Dublin, OH (US); Anne C. Voss, Columbus, OH (US); Maria G. Baggs, Columbus, OH (US); Charles L. Paule, Westerville, OH (US); Refaat A. Hegazi, Dublin, OH (US); Fabrizis Suarez, New Albany, OH (US); Gary Fanjiang, Gahanna, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 14/371,905

(22) PCT Filed: Jan. 10, 2013

(86) PCT No.: PCT/US2013/021029
§ 371 (c)(1),
(2) Date: Jul. 11, 2014

(87) PCT Pub. No.: WO2013/106570
PCT Pub. Date: Jul. 18, 2013

(65) Prior Publication Data
US 2015/0133548 A1 May 14, 2015

Related U.S. Application Data

(60) Provisional application No. 61/585,265, filed on Jan. 11, 2012.

(51) Int. Cl.
| | | |
|---|---|---|
| *A01N 37/02* | (2006.01) | |
| *A61K 31/22* | (2006.01) | |
| *A61K 31/19* | (2006.01) | |
| *A61K 31/198* | (2006.01) | |
| *A61K 9/00* | (2006.01) | |
| *A61K 9/127* | (2006.01) | |
| *A23L 33/10* | (2016.01) | |
| *A23L 33/175* | (2016.01) | |

(52) U.S. Cl.
CPC .............. *A61K 31/22* (2013.01); *A23L 33/10* (2016.08); *A23L 33/175* (2016.08); *A61K 9/0019* (2013.01); *A61K 9/127* (2013.01); *A61K 9/1272* (2013.01); *A61K 31/19* (2013.01); *A61K 31/198* (2013.01); *A23V 2002/00* (2013.01)

(58) Field of Classification Search
CPC ........ A61K 31/19; A61K 31/59; A61K 36/66; A61K 36/539
See application file for complete search history.

(56) References Cited

U.S. PATENT DOCUMENTS 6,031,000 A    2/2000 Nissen et al.

OTHER PUBLICATIONS

University of North Carolina, School of Medicine, Pivotal Trial of Dermagraft® to treat diabetic foot ulcer, Aug. 2010.*
Group Health 2010..*
Leaphart et al, Case management Resource Path on Chronic Wound Care, 2005.*
Frykberg et al, Diabetic Foot Disorders a clinical Practice Guideline (2006 version).*
Ballmer et al, Clinical Nutrition (201) 20(3);271-273.*
International Search Report and Written Opinion for PCT/US2013/021029 dated Mar. 25, 2013.
International Preliminary Report on Patentability for PCT/US2013/021029 dated Jul. 15, 2014.
Communication Pursuant to Rules 161(1) & 162 EPC for EP Patent Application No. 13700442.0 dated Aug. 20, 2014.
Anonymous, "Abound", Internet 2010—retrieved from the Internet URL:http://abound.net on Feb. 20, 2013.
Anonymous, "Abound—Product Monograph," Internet 2008—retrieved from Internet URL:http://abbott.vo.llnwd.net/018/abound/local/pdf/e00155_abound_monograph_vf_3.pdf (retrieved Feb. 20, 2013).
Tatti, et al., "Effect of a nutritional supplement used for diabetic foot ulcers on microalbuminuria," Mediterranean Journal of Nutrition and Metabolism: Official Journal of the Italian Association for Dietetics and Clinical Nutrition (ADI) a Member of the Italian Federation of Nutritional Societies (FESIN), Springer Milan, Milan, vol. 5, No. 1, Aug. 11, 2011, pp. 67-69.
Tatti, et al., "Nutritional supplement is associated with a reduction in healing time and improvement of fat free body mass in patients with diabetic food ulcers," EWMA Journal, vol. 10, No. 3, 2010, pp. 13-18.
Office Action from VN Patent Application No. 1-2014-02218 dated Sep. 16, 2014.

(Continued)

*Primary Examiner* — Jean P Cornet

(57) ABSTRACT

Disclosed is the combination of beta-hydroxy-beta-methylbutyrate, arginine, and glutamine for use in a method of treating a diabetic ulcer in a diabetic individual having at least one of: (a) a serum albumin level of less than or equal to 4.0 g/dL, and/or (b) an Ankle-Brachial Index of less than 1.0. 9. Also disclosed is the use of the combination of beta-hydroxy-beta-methylbutyrate, arginine, and glutamine for the manufacture of a medicament for use in the treatment of a diabetic ulcer in a diabetic individual having at least one of: (a) a serum albumin level of less than or equal to 4.0 g/dL, and/or (b) an Ankle-Brachial Index of less than 1.0. In certain embodiments, the combination of beta-hydroxy-beta-methylbutyrate, arginine, and glutamine are orally administered via a nutritional composition.

20 Claims, No Drawings

(56) References Cited

OTHER PUBLICATIONS

Tatti et al., "The Use of a Specialized Nutritional Supplement for Diabetic Foot Ulcers Reduces the Use of Antibiotics," J. Endocrinol. Metab. (2012), vol. 2, No. 1, pp. 26-31.
Office Action in CA Application No. 2,860,642 dated May 12, 2015.
Written Opinion for SG Application No. 11201403951 dated Apr. 20, 2015 (received May 26, 2015).

* cited by examiner

COMBINATION OF BETA-HYDROXY-BETA-METHYLBUTYRATE, ARGININE AND GLUTAMINE FOR USE IN TREATING DIABETIC ULCERS

CROSS-REFERENCE TO RELATED APPLICATIONS

This application is the U.S. national stage entry of International Application No. PCT/US2013/021029, filed Jan. 10, 2013, which claims priority to and any other benefit of U.S. Provisional Application Ser. No. 61/585,265, filed on Jan. 11, 2012, the contents of which are incorporated by reference herein in their entirety.

FIELD OF THE DISCLOSURE

The present disclosure is directed to methods of promoting the healing of diabetic ulcers in diabetic individuals who are malnourished and/or who have a reduced blood flow to the lower extremities using a nutritional composition including beta-hydroxy-beta-methylbutyrate in combination with arginine and glutamine. More particularly, the present disclosure is directed to methods of promoting the healing of diabetic ulcers in diabetic individuals who have an albumin level of less than or equal to 4.0 g/dL, an Ankle-Brachial Index of less than 1.0, or both.

BACKGROUND OF THE DISCLOSURE

Diabetes mellitus is a disorder of carbohydrate metabolism resulting from insufficient production of, or reduced sensitivity to, insulin. In persons who have diabetes, the normal ability of body cells to use glucose is inhibited, thereby increasing blood sugar levels. As more glucose accumulates in the blood, excess levels of sugar are excreted in the urine. Corresponding symptoms of diabetes include increased urinary volume and frequency, thirst, hunger, weight loss, and weakness.

There are two variations of diabetes. Type 1 diabetes is insulin dependent diabetes mellitus for which insulin administration is required. In a subject patient with type 1 diabetes, insulin is not secreted by the pancreas and therefore must be taken by injection or inhalation. Type 2 diabetes may be controlled by dietary restriction, oral anti-hyperglycemic agents, and/or insulin administration. Type 2 diabetes can be attributable to dilatory pancreatic secretion of insulin and reduced sensitivity to the action of insulin on target tissues.

One significant issue that many diabetics face is the unwanted formation of diabetic ulcers, which typically form on the lower extremities, such as on the feet. Diabetic ulcers are open wounds that form on the surface of the skin and can be extremely difficult to heal and close, especially for those diabetics that are poorly nourished or malnourished and/or have decreased blood flow to the lower extremities, including decreased blood flow to the feet. Even when an accepted standard of care is given to a diabetic with a diabetic ulcer (sufficient wound cleansing and dressing replacement, etc.) many diabetics require additional assistance to sufficiently heal and close these types of wounds.

To date, such diabetic ulcers have been treated with numerous pharmaceutical-based therapies, devices, and nutritional compositions. Generally, the nutritional compositions have included antioxidants, zinc, and protein in an attempt to further wound healing. Although some of these approaches have had moderate success, none have proven sufficient to fully address the problem.

As such, there is a need for an alternative to pharmacological therapy and device therapy for treating and improving the rate of healing and closure of diabetic ulcers in diabetic individuals. Nutritional compositions and methods for treating and improving the rate of healing of the diabetic ulcers would be particularly beneficial.

SUMMARY OF THE DISCLOSURE

The present disclosure is directed to methods of promoting the healing of diabetic ulcers, including diabetic foot ulcers, in individuals having diabetes who are malnourished and/or have a reduced blood flow to the lower extremities, including a reduced blood flow to the feet. The diabetic individuals may have a serum albumin level of less or equal to 4.0 g/dL, which indicates that they are at risk of malnutrition, and/or may have an Ankle Brachial Index of less than 1.0, which indicates that the individual may have reduced blood flow in the feet. The methods described herein utilize a nutritional composition including beta-hydroxy-beta-methylbutyrate, arginine, and glutamine that is administered to the diabetic individual to promote the healing of the diabetic ulcer.

One embodiment is directed to a method of promoting the healing of a diabetic ulcer in a diabetic individual having a serum albumin level of less than or equal to 4.0 g/dL. The method comprises administering to the individual a nutritional composition comprising beta-hydroxy-beta-methylbutyrate, arginine, and glutamine.

Another embodiment is directed to a method of promoting the healing of a diabetic ulcer in a diabetic individual having an Ankle-Brachial Index of less than 1.0. The method comprises administering to the individual a nutritional composition comprising beta-hydroxy-beta-methylbutyrate, arginine, and glutamine.

Another embodiment is directed to a method of promoting the healing of a diabetic ulcer in a diabetic individual having a serum albumin level of less than or equal to 4.0 g/dL and an Ankle-Brachial Index of less than 1.0. The method comprises administering to the individual a nutritional composition comprising beta-hydroxy-beta-methylbutyrate, arginine, and glutamine.

Another embodiment is directed to a method of promoting the healing of a diabetic ulcer in a malnourished diabetic individual. The method comprises administering to the malnourished diabetic individual a nutritional composition comprising beta-hydroxy-beta-methylbutyrate, arginine, and glutamine.

Another embodiment is directed to a method of promoting the healing of a diabetic ulcer in a diabetic individual having a reduced blood flow to the lower extremities. The method comprises administering to the individual a nutritional composition comprising beta-hydroxy-beta-methylbutyrate, arginine, and glutamine.

Another embodiment is directed to a method of promoting the healing of a diabetic ulcer in a malnourished diabetic individual having a reduced blood flow to the lower extremities. The method comprises administering to the individual a nutritional composition comprising beta-hydroxy-beta-methylbutyrate, arginine, and glutamine.

It has been unexpectedly found that the administration of a nutritional composition including a combination of beta-hydroxy-beta-methylbutyrate, arginine and glutamine significantly promotes the healing of diabetic ulcers, and specifically diabetic foot ulcers in diabetic individuals that are malnourished, at risk of becoming malnourished, and/or have a reduced blood flow to the lower extremities. In some embodiments, the diabetic individual will have a serum albumin level of less than or equal to 4.0 g/dL and/or an Ankle-Brachial Index of less than 1.0. These surprising findings show that this nutritional composition is capable of promoting the healing of diabetic ulcers in diabetic individuals that are either malnourished and/or have reduced blood flow to the lower extremities. Surprisingly, the nutritional compositions promote the healing of the diabetic ulcer without changing or impacting the nourishment or blood flow of the diabetic individual.

Accordingly, the nutritional compositions and methods of the present disclosure may offer an alternative, or supplemental, therapeutic option that may promote the healing of diabetic ulcers in diabetic individuals. These benefits may be advantageously achieved without the complications seen with the previously used oral synthetic pharmacological approaches.

DETAILED DESCRIPTION OF THE DISCLOSURE

The present disclosure is directed to methods of facilitating and/or promoting the healing of diabetic ulcers, and specifically diabetic foot ulcers, in diabetic individuals that either have Type I or Type II diabetes, and that are malnourished, at risk of becoming malnourished, and/or have a reduced blood flow to the lower extremities, including a reduced blood flow to the feet. In some embodiments, the methods are directed toward the healing of diabetic ulcers in diabetic individuals that have a serum albumin level of less than or equal to 4.0 g/dL and/or an Ankle-Brachial Index of less than 1.0 and utilize a nutritional composition that includes beta-hydroxy-beta-methylbutyrate, arginine, and glutamine. Diabetic individuals that meet one or both of these criteria are either malnourished, at risk of becoming malnourished, and/or have a reduced blood flow to the lower extremities. As such, these diabetic individuals are at increased risk for getting diabetic ulcers, such as diabetic foot ulcers as they do not generally maintain a healthy lifestyle. Once a diabetic individual gets a diabetic ulcer, such as a diabetic foot ulcer, it can be very difficult to completely heal and close the ulcer, even when an appropriate standard of care is given.

The nutritional compositions and methods disclosed herein offer a nutritional solution to the longstanding problem of diabetic ulcers in diabetic individuals, and particularly to diabetic foot ulcers that can be particularly problematic. The methods disclosed herein offer an alternative therapeutic option that does not require pharmaceutical drugs or devices and that can be utilized to promote the healing of the diabetic ulcer in a timely and consistent manner. While addressing the healing of the diabetic ulcer, the nutritional compositions of the present disclosure do not impact the serum albumin level and/or the lower extremity blood flow of the diabetic individual.

These and other optional elements or features of the various embodiments of the present disclosure are described in detail hereafter.

The term "promoting the healing" as used herein, unless otherwise specified, refers to facilitating the healing or improving the rate of healing of a diabetic ulcer wound, such as a diabetic foot ulcer wound, such that the diabetic ulcer wound is closed and healed.

The terms "diabetic ulcer" or "neuropathic ulcer" as used herein, unless otherwise specified, refer to an ulcer, including ulcers of the lower extremities, that are associated with diabetes in a diabetic individual. One specific example of a diabetic ulcer is a diabetic foot ulcer.

The terms "diabetic" or "diabetic individual" as used herein, unless otherwise specified, refer to an individual that has either type I or type II diabetes.

The terms "nutritional composition" and "nutritional formula" as used herein, unless otherwise specified, are used interchangeably to refer to nutritional liquids, nutritional powders, nutritional solids, nutritional semi-solids and nutritional semi-liquids that are suitable for oral administration to a human. The nutritional compositions may represent a sole, primary, or supplemental source of nutrition.

The term "nutritional liquid," as used herein, unless otherwise specified, refers to nutritional products in ready-to-drink liquid form, concentrated form, and nutritional liquids made by reconstituting the nutritional powders described herein prior to use.

The term "nutritional powder," as used herein, unless otherwise specified, refers to nutritional products in flowable or scoopable form that can be reconstituted with water or another aqueous liquid prior to consumption and includes both spray dried and drymixed/dryblended powders.

The term "nutritional semi-solid," as used herein, unless otherwise specified, refers to nutritional products that are intermediate in properties, such as rigidity, between solids and liquids. Some semi-solid examples include puddings, gelatins, and doughs.

The term "nutritional semi-liquid," as used herein, unless otherwise specified, refers to nutritional products that are intermediate in properties, such as flow properties, between liquids and solids. Some semi-liquid examples include thick shakes and liquid gels.

The terms "retort" and "retort sterilized" are used interchangeably herein, and unless otherwise specified, refer to the common practice of filling a container, most typically a metal can or other similar package, with a nutritional liquid and then subjecting the liquid-filled package to the necessary heat sterilization step, to form a retort sterilized nutritional liquid product.

The terms "aseptic" and "aseptic sterilized" are used interchangeably herein, and unless otherwise specified, refer to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to fat or lipid materials derived or processed from plants or animals. These terms also include synthetic fat or lipid materials so long as such synthetic materials are suitable for oral administration to humans.

All percentages, parts and ratios as used herein, are by weight of the total product, unless otherwise specified. All such weights as they pertain to listed ingredients are based on the active level and, therefore, do not include solvents or by-products that may be included in commercially available materials, unless otherwise specified.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The various embodiments of the nutritional compositions of the present disclosure may also be substantially free of any optional or selected ingredient or feature described herein, provided that the remaining nutritional composition still contains all of the required ingredients or features as described herein. In this context, and unless otherwise specified, the term "substantially free" means that the selected composition contains less than a functional amount of the optional ingredient, typically less than about 1%, including less than about 0.5%, including less than about 0.1%, and also including zero percent, by weight of such optional or selected essential ingredient.

The nutritional compositions and methods described herein may comprise, consist of, or consist essentially of the elements of the products or methods as described herein, as well as any additional or optional element described herein or otherwise useful in nutritional product applications.

Methods of Promoting the Healing of Diabetic Ulcers in Diabetic Individuals

The multiple methods of the present disclosure provide certain, defined subclasses of diabetic individuals with many options for promoting the healing of diabetic ulcers, including diabetic foot ulcers, by administering to the diabetic individual a nutritional composition as described herein. The methods of the present disclosure are particularly applicable to diabetic individuals who are malnourished, or who are at risk of being malnourished, diabetic individuals who have a reduced blood flow to the lower extremities, including a reduced blood flow to the feet, and diabetic individuals who are malnourished (or at risk of becoming malnourished) and have a reduced blood flow to the lower extremities. Whether a diabetic individual is malnourished, at risk of being malnourished, and/or has a reduced blood flow to the lower extremities (as compared to a non-diabetic, healthy individual), including a reduced blood flow to the feet, can be readily determined by one skilled in the art.

Diabetic ulcers, and particularly diabetic foot ulcers, may occur in diabetic individuals as a result of many factors, such as mechanical changes in the conformation of the bony architecture of the foot, peripheral neuropathy, and peripheral arterial disease, all of which occur with higher frequency in the diabetic population. The treatment and/or promotion of healing, including the promotion of healing to full wound closure, of all types of diabetic ulcers are within the scope of the present disclosure. In one particular embodiment, the present disclosure is directed to the treatment and/or promotion of healing, including the promotion of healing to full closure of the wound, of diabetic foot ulcers.

The methods described herein utilize a nutritional composition that is administered to the diabetic individual as described further herein to promote the healing of the diabetic ulcer. In one embodiment, the nutritional composition includes beta-hydroxy-beta-methylbutyrate, glutamine, and arginine. The beta-hydroxy-beta-methylbutyrate is desirably present as calcium beta-hydroxy-beta-methylbutyrate. The nutritional compositions as described herein may also include one or more additional nutritional ingredients such as protein, carbohydrate, fat, vitamins, minerals, and the like along with other optional ingredients such as sweeteners.

In some embodiments of the present disclosure the diabetic individual administered the nutritional composition as described herein has a serum albumin level that is indicative of the diabetic individual being malnourished, or at risk of being malnourished. A serum albumin test measures the amount of this protein in the clear liquid portion of the blood. In some embodiments of the present disclosure, the diabetic individual has a serum albumin level of less than or equal to 4.0 g/dL, or even less than or equal to 3.7 g/dL, or even less than or equal to 3.5 g/dL, or even less than or equal to 3.0 g/dL, or even less than or equal to 2.7 g/dL, or even less than or equal to 2.5 g/dL, or even less than or equal to 2.2 g/dL, or even less than or equal to 2.0 g/dL. In some embodiments, the serum albumin level in the diabetic individual may be from about 2.0 g/dL to less than or equal to 4.0 g/dL, or even from about 2.0 g/dL to about 3.5 g/dL, or even from about 2.0 g/dL to about 3.0 g/dL. Serum albumin levels of less than or equal to 4.0 g/dL are generally indicative of the body not absorbing and digesting sufficient amounts of protein and indicate a status of malnutrition in an individual, including in a diabetic individual. Malnourishment in a diabetic individual can be particularly problematic as the individual's body is already in a diabetic state, and malnourishment only serves to further degrade the overall health of the individual and make wound healing even more difficult. By being malnourished, the diabetic individual is overall more prone to getting diabetic ulcers, and particularly diabetic foot ulcers.

In some other embodiments of the present disclosure the diabetic individual administered the nutritional composition as described herein has an Ankle-Brachial Index (ABI) that is indicative of the diabetic individual having reduced blood flow to the lower extremities, including reduced blood flow to the feet. The ABI is the ratio of the blood pressure in the lower legs to the blood pressure in the arms. Compared to the arm, lower blood pressure in the leg is an indication of blocked arteries (peripheral vascular disease). The ABI is calculated by dividing the systolic blood pressure at the ankle by the systolic blood pressures in the arm. Many diabetics have a low ABI, which results in reduced blood flow to the lower extremities, which can promote the formation of diabetic ulcers, and particularly diabetic foot ulcers. In some embodiments of the present disclosure, the diabetic individual has an ABI of less than 1.0, or even less than 0.9, or even less than 0.8, or even less than 0.7, or even less than 0.6, or even less than 0.5, or even less than 0.4, or even less than 0.3. In some embodiments, the diabetic individual may have an ABI of from about 0.3 to 1.0, or even from about 0.3 to about 0.9, or even from about 0.3 to about 0.8, or even from about 0.3 to about 0.7, or even from about 0.3 to about 0.6, or even from about 0.3 to about 0.5. In other embodiments, the diabetic individual may have an ABI of 0.2, or 0.3, or even 0.4, or even 0.5, or even 0.6, or even 0.7, or even 0.8, or even 0.9.

ABI levels of less than 1.0 are generally indicative of a reduced blood flow to the lower extremities, and specifically a reduced blood flow to the feet in an individual, including in a diabetic individual. A reduced blood flow in the lower extremities in a diabetic individual can be particularly problematic as the individual's body is already in a diabetic state, and reduced blood flow only serves to further degrade the overall health of the individual and make wound healing more difficult. By having a reduced blood flow in the lower extremities, the diabetic individual is overall more prone to getting diabetic ulcers, and particularly diabetic foot ulcers.

In some other embodiments of the present disclosure, the diabetic individual administered the nutritional composition as described herein has a serum albumin level that is indicative of the diabetic individual being malnourished, or at risk of being malnourished and has an Ankle-Brachial Index (ABI) that is indicative of the diabetic individual having reduced blood flow to the lower extremities, including reduced blood flow to the feet. In these embodiments, the diabetic individual is at an increased risk for diabetic ulcers, and specifically diabetic foot ulcers, as the individual is both malnourished, or at risk of being malnourished, and has reduced blood flow to the lower extremities. In these embodiments, the diabetic individual has a serum albumin level of less than or equal to 4.0 g/dL, or even less than or equal to 3.7 g/dL, or even less than or equal to 3.5 g/dL, or even less than or equal to 3.0 g/dL, or even less than or equal to 2.7 g/dL, or even less than or equal to 2.5 g/dL, or even less than or equal to 2.2 g/dL, or even less than or equal to 2.0 g/dL. In some embodiments, the serum albumin level in the diabetic individual may be from about 2.0 g/dL to less than or equal to 4.0 g/dL, or even from about 2.0 g/dL to about 3.5 g/dL, or even from about 2.0 g/dL to about 3.0 g/dL and has an ABI of less than 1.0, or even less than 0.9, or even less than 0.8, or even less than 0.7, or even less than 0.6, or even less than 0.5, or even less than 0.4, or even less than 0.3. In some embodiments, the diabetic individual may have an ABI of from about 0.3 to 1.0, or even from about 0.3 to about 0.9, or even from about 0.3 to about 0.8, or even from about 0.3 to about 0.7, or even from about 0.3 to about 0.6, or even from about 0.3 to about 0.5. In other embodiments, the diabetic individual may have an ABI of 0.2, or 0.3, or even 0.4, or even 0.5, or even 0.6, or even 0.7, or even 0.8, or even 0.9.

In accordance with the methods of the present invention, to promote the healing of the diabetic ulcer, and in particular the diabetic foot ulcer, in the diabetic individual that has a serum albumin level of less than or equal to 4.0 g/dL and/or an ABI of less than 1.0, the diabetic individual is desirably administered the nutritional composition including beta-hydroxy-beta-methylbutyrate, glutamine, and arginine as described herein for a time period of at least 1 week, or even at least 2 weeks, or even at least 3 weeks, or even at least 4 weeks, or even at least 5 weeks, or even at least 6 weeks, or even at least 7 weeks, or even at least 8 weeks, or even at least 9 weeks, or even at least 10 weeks, or even at least 11 weeks, or even at least 12 weeks, or even at least 14 weeks, or even at least 16 weeks, or even at least 18 weeks, or even at least 24 weeks or longer. In some embodiments, the diabetic individual is administered the nutritional composition continuously for 6 months, or even 12 months, or even 18 months, or even 24 months or longer, including continuous administration for the life of the diabetic individual. In one particular embodiment, the diabetic individual is administered the nutritional composition for about 16 weeks.

During the period of administration as described above, the diabetic individual desirably consumes at least one serving of the nutritional composition daily, and in some embodiments, may consume two, three, four or even more servings per day. In a desirable embodiment, the diabetic individual consumes two servings of the nutritional composition per day to receive the desired amount of beta-hydroxy-beta-methylbutyrate, glutamine, and arginine. Each serving is desirably administered as a single, undivided dose, although the serving may also be divided into two or more partial or divided servings to be taken at two or more times during the day. The methods of the present disclosure include continuous day after day administration, as well as periodic or limited administration, although continuous day after day administration is generally desirable. The methods of the present disclosure are preferably applied on a daily basis, desirably as a long term, continuous, daily, dietary supplement.

Product Form

The nutritional compositions used in the methods of the present disclosure include beta-hydroxy-beta-methylbutyrate (HMB), typically in the form of calcium HMB, in combination with glutamine and arginine. The nutritional compositions may be formulated and administered in any known or otherwise suitable oral product form, so long as they include HMB, glutamine, and arginine. Any solid, liquid, semi-solid, semi-liquid or powder form, including combinations or variations thereof, are suitable for use in the methods described herein, provided that such forms allow for safe and effective oral delivery to the diabetic individual of the ingredients as also defined herein. In one particularly desirable embodiment, the nutritional composition is a nutritional powder that is admixed with water to form a reconstituted liquid that is consumed.

Nutritional Liquids

Nutritional liquids include both concentrated and ready-to-feed nutritional liquids, and will include HMB, glutamine, and arginine as detailed herein. These nutritional liquids are most typically formulated as suspensions or emulsions, although other liquid forms are within the scope of the present disclosure.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to about 95% by weight of water, including from about 50% to about 95%, also including from about 60% to about 90%, and also including from about 70% to about 85%, by weight of water. The nutritional emulsions may have a variety of product densities, but most typically have a density greater than about 1.03 g/mL, including greater than about 1.04 g/mL, including greater than about 1.055 g/mL, including from about 1.06 g/mL to about 1.12 g/mL, and also including from about 1.085 g/mL to about 1.10 g/mL.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the emulsion may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

The nutritional emulsions may have a pH ranging from about 3.5 to about 8, but are most advantageously in a range of from about 4.5 to about 7.5, including from about 4.5 to about 7.0, including from about 4.5 to about 6.5, including from about 4.5 to about 6.0, and including from about 4.5 to about 5.5. In some embodiments, the pH may be from about 5.5 to about 7.3, including from about 5.5 to about 7.0, including from about 5.5 to about 6.5, and including from about 5.5 to about 6.0. In other embodiments, the pH may be from about 6.2 to about 7.2, including from about 6.2 to about 7.0, including from about 6.2 to about 6.8, and further including from about 6.2 to about 6.5.

Although the serving size for the nutritional emulsion can vary depending upon a number of variables, a typical serving size is generally at least about 1 mL, or even at least about 2 mL, or even at least about 5 mL, or even at least about 10 mL, or even at least about 25 mL, including ranges from about 2 mL to about 300 mL, including from about 4 mL to about 250 mL, and including from about 10 mL to about 240 mL.

Nutritional Solids

The nutritional solids may be in any solid form, but are typically in the form of flowable or substantially flowable particulate compositions, and will include HMB, glutamine, and arginine as detailed herein. Particularly suitable nutritional solid product forms include spray dried, agglomerated and/or dryblended powder compositions. The compositions can easily be scooped and measured with a spoon or similar other device, or packaged in single or multiple serving packages, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the reconstituted powder may have a caloric density of from about 50-100 kcal/liter to about 660 kcal/liter, including from about 150 kcal/liter to about 500 kcal/liter. In some specific embodiments, the reconstituted powder may have a caloric density of 25, or 50, or 75, or 100 kcal/liter.

Other nutritional solids include nutritional bites (e.g., plurality of smaller dietary product dosage forms in a single package) and nutritional bars (snack or meal replacement) as known in the nutrition art. In one particularly desirable embodiment, the nutritional composition includes HMB, glutamine, and arginine in powdered form in a single serving packet that can be mixed with water, or another liquid (e.g., juice, tea, etc.) and consumed.

Beta-Hydroxy-Beta-Methylbutyrate (HMB)

The nutritional compositions comprise HMB, which means that the compositions are either formulated with the addition of HMB, most typically as a calcium monohydrate, or are otherwise prepared so as to contain HMB in the finished product. Any source of HMB is suitable for use herein provided that the finished product contains HMB, although such a source is preferably calcium HMB and is most typically added as such to the nutritional products during formulation.

Although calcium HMB monohydrate is the preferred source of HMB for use herein, other suitable sources may include HMB as a free acid, a salt, an anhydrous salt, an ester, a lactone, or other product forms that otherwise provide a bioavailable form of HMB from the nutritional product. Non-limiting examples of suitable salts of HMB for use herein include HMB salts, hydrated or anhydrous, of sodium, potassium, magnesium, chromium, calcium, or other non-toxic salt form. Calcium HMB monohydrate is preferred and is commercially available from Technical Sourcing International (TSI) (Salt Lake City, Utah) and from Lonza Group Ltd. (Basel, Switzerland).

When the nutritional product is a liquid, the concentration of HMB in the liquid may range up to 15%, including from about 0.1% to about 10%, including from about 0.1% to about 8%, and also including from about 0.1% to about 7%, and also including from about 0.1% to about 5%, and also including from about 0.3% to about 3%, and also including from about 0.4% to about 1.5%, by weight of the liquid composition. In one specific embodiment the HMB is present in the liquid composition in an amount of from about 0.1% to about 0.5% by weight of the nutritional liquid.

When the nutritional product is a solid or powder, the concentration of HMB in the solid or powder may range up to about 15%, including from about 0.1% to about 10%, and also including from about 0.1% to about 2%, and also including from about 0.2% to about 5%, and also including from about 0.3% to about 3%, and also including from about 0.4% to about 1.5%, by weight of the nutritional solid or powder. In a specific embodiment, the HMB is present in the solid or powder composition in an amount of from about 0.1% to about 0.5% by weight of the nutritional composition. In another specific embodiment, the HMB is present in the solid or powder composition in an amount of from about 3.0% to about 7.0%, including from about 3.0% to about 6.5%, and including from about 3.0% to about 6.0% by weight of the nutritional solid or powder. In another specific embodiment, the HMB is present in the nutritional solid or powder in an amount of from about 3.0% to about 6.7%, including from about 3.5% to about 6.7%, and also including from about 4.0% to about 6.7%, and also including from about 4.5% to about 6.7%, and also including from about 5.0% to about 6.7%, and also including about 6.7% by weight of the nutritional solid or powder.

The nutritional compositions are formulated with sufficient HMB to allow diabetic individual administered the nutritional composition to receive a sufficient amount of HMB daily to promote the healing of diabetic ulcers, including diabetic foot ulcers. In some embodiments, the diabetic individual will have a daily intake of HMB of from about 1.0 to about 10 grams, including from about 2.0 to about 9.0 grams, including from about 2.0 to about 8.0 grams, including from about 2.0 to about 7.0 grams, including from about 2.0 to about 6.0 grams, including from about 2.0 to about 5.0 grams, including from about 2.0 to about 4.0 grams, and including from about 2.0 to about 3.0 grams. In one specific embodiment, the diabetic individual receives about 2.4 grams per day of HMB. In another specific embodiment, the diabetic individual receives about 1.2 grams per day of HMB.

Amino Acids Glutamine and Arginine

In addition to the HMB described above, the nutritional compositions described herein for use by the diabetic individual include both of the amino acids glutamine and arginine. Any source of glutamine and arginine that provides the desired amounts of the amino acids in the nutritional compositions is acceptable, although it is generally desirable that the glutamine and arginine be present in the nutritional compositions as free amino acids in the L- or D-configuration, with the L-glutamine and L-arginine forms being particularly desirable. The amount of glutamine and arginine present in the nutritional compositions of the present disclosure may be the same amount, or may be different amounts. Additional amino acids may also be added to the nutritional compositions of the present disclosure.

When the nutritional product is a liquid, the concentrations of glutamine and arginine, independently, in the liquid may range up to 45%, including from about 5.0% to about 45%, including from about 10% to about 45%, and also including from about 10% to about 42% by weight of the liquid composition. In some embodiments, the amount of glutamine and the amount of arginine, independently, may be from about 10% to about 45%, and also including from about 10% to about 40%, and also including from about 20% to about 35%, and also including from about 20% to about 32% by weight of the liquid composition. In one specific embodiment the glutamine is present in an amount of about 32% and the arginine is present in an amount of about 31% by weight of the liquid composition.

When the nutritional product is a solid or powder, the concentration of glutamine and arginine, independently, in the solid or powder may range up to about 45%, including from about 5% to about 45%, and also including from about 10% to about 45% and also including from about 15% to about 45%, and also including from about 20% to about 45%, and also including from about 25% to about 40%, by weight of the nutritional solid or powder. In a specific embodiment, the concentration of glutamine and arginine, independently, in the solid or powder is from about 10% to about 40%, including from about 20% to about 35%, and including from about 30% to about 35%, and including from about 30% to about 34%, and including from about 30% to about 33%, and including from about 30% to about 32%, by weight of the nutritional solid or powder. In one specific embodiment, the glutamine is present in the nutritional solid or powder in an amount of about 32% and the arginine is present in an amount of about 31%, by weight of the nutritional solid or powder.

The nutritional compositions are formulated with sufficient glutamine and arginine to allow the diabetic individual administered the nutritional composition to receive a sufficient amount of glutamine and arginine daily to promote the healing of diabetic ulcers, including diabetic foot ulcers. In some embodiments, the diabetic individual will have a daily intake of glutamine and arginine, independently, of from about 1.0 to about 20 grams, including from about 2.0 to about 20 grams, including from about 3.0 to about 20 grams, including from about 4.0 to about 20 grams, including from about 5.0 to about 20 grams, including from about 10 to about 20 grams, including from about 10 to about 15 grams, and including from about 10 to about 14 grams. In one specific embodiment, the diabetic individual receives about 14 grams per day of glutamine and about 14 grams per day of arginine.

In one specific embodiment of the present disclosure, the nutritional composition is a powdered nutritional composition that includes from about 20% to about 35% by weight arginine, from about 20% to about 35% by weight glutamine, and from about 3.0% to about 7.0% by weight calcium HMB. In another specific embodiment of the present disclosure, the nutritional composition is a powdered nutritional composition that includes about 31% by weight arginine, about 32% by weight glutamine, and about 6.7% by weight calcium HMB.

In another specific embodiment, the nutritional composition provides the diabetic individual from about 10 to about 15 grams per day of glutamine, from about 10 to about 15 grams per day of arginine, and from about 2 to about 5 grams per day of HMB. In another specific embodiment, the nutritional composition provides the diabetic individual about 14 grams per day of arginine, about 14 grams per day of glutamine, and about 2.4 grams per day of HMB.

Macronutrients

The nutritional compositions of the present disclosure may optionally in some embodiments further comprise one or more optional macronutrients in addition to the HMB, glutamine, and arginine described herein. The optional macronutrients include proteins, fats, carbohydrates, and combinations thereof.

Macronutrients suitable for use herein include any protein, fat, or carbohydrate or source thereof that is known for or otherwise suitable for use in an oral nutritional composition, provided that the optional macronutrient is safe and effective for oral administration and is otherwise compatible with the other ingredients in the nutritional composition.

In some embodiments, carbohydrate concentrations most typically range from about 5% to about 40%, including from about 5% to about 35%, including from about 5% to about 30%, including from about 7% to about 30%, including from about 10% to about 30%, including from about 10% to about 25%, by weight of the nutritional composition; fat concentrations most typically range from about 0.5% to about 30%, from about 0.5% to about 25%, including from about 0.5% to about 20%, including from about 0.75% to about 20%, including from about 1% to about 15%, including from about 1% to about 10%, and also including from about 2% to about 5%, by weight of the nutritional composition; and protein concentrations most typically range from about 5% to about 85%, including from about 5% to about 75%, including from about 5% to about 70%, including from about 5% to about 60%, including from about 7% to about 50%, and also including from about 8% to about 32%, by weight of the nutritional composition.

The concentration or amount of optional fat, carbohydrate, and protein in the nutritional composition can vary considerably depending upon the particular product form (e.g., bars or other solid dosage forms, milk or soy-based liquids or other clear beverages, reconstitutable powders, etc.) and the various other formulations and targeted dietary needs. In some embodiments, these optional macronutrients may be formulated within any of the embodied ranges described in the following tables.

| Nutrient (% total calories) | Example A | Example B | Example C |
|---|---|---|---|
| Carbohydrate | 0-100 | 10-70 | 40-50 |
| Fat | 0-100 | 20-65 | 35-55 |
| Protein | 0-100 | 5-40 | 15-25 |

Each numerical value preceded by the term "about"

| Nutrient (wt % composition) | Example D | Example E | Example F |
|---|---|---|---|
| Carbohydrate | 0-98 | 1-50 | 10-30 |
| Fat | 0-98 | 1-30 | 3-15 |
| Protein | 0-98 | 1-30 | 2-10 |

Each numerical value preceded by the term "about"

Carbohydrate

Optional carbohydrates suitable for use in the nutritional compositions may be simple, complex, or variations or combinations thereof. Non-limiting examples of suitable carbohydrates include hydrolyzed or modified starch or cornstarch, maltodextrin, isomaltulose, sucromalt, glucose polymers, sucrose, corn syrup, corn syrup solids, rice-derived carbohydrate, glucose, fructose, lactose, high fructose corn syrup, honey, sugar alcohols (e.g., maltitol, erythritol, sorbitol), and combinations thereof.

Optional carbohydrates suitable for use herein also include soluble dietary fiber, non-limiting examples of which include gum Arabic, fructooligosaccharide (FOS), sodium carboxymethyl cellulose, guar gum, citrus pectin, low and high methoxy pectin, oat and barley glucans, carrageenan, psyllium, and combinations thereof. Insoluble dietary fiber is also suitable as a carbohydrate source herein, non-limiting examples of which include oat hull fiber, pea hull fiber, soy hull fiber, soy cotyledon fiber, sugar beet fiber, cellulose, corn bran, and combinations thereof.

Protein

Optional proteins suitable for use in the nutritional compositions include hydrolyzed, partially hydrolyzed or non-hydrolyzed proteins or protein sources, and can be derived from any known or otherwise suitable source such as milk (e.g., casein, whey), animal (e.g., meat, fish, egg albumen), cereal (e.g., rice, corn), vegetable (e.g., soy, pea, potato), or combinations thereof. The proteins for use herein can also include, or be entirely or partially replaced by, free amino acids known for use in nutritional products, non-limiting examples of which include L-tryptophan, L-glutamine, L-tyrosine, L-methionine, L-cysteine, taurine, L-arginine, L-carnitine, and combinations thereof.

Fat

Optional fats suitable for use in the nutritional compositions include coconut oil, fractionated coconut oil, soy oil, corn oil, olive oil, safflower oil, high oleic safflower oil, high GLA-safflower oil, MCT oil (medium chain triglycerides), sunflower oil, high oleic sunflower oil, palm and palm kernel oils, palm olein, canola oil, flaxseed oil, borage oil, cottonseed oils, evening primrose oil, blackcurrant seed oil, transgenic oil sources, fungal oils, marine oils (e.g., tuna, sardine), and so forth.

Optional Ingredients

The nutritional compositions may further comprise other optional ingredients that may modify the physical, nutritional, chemical, hedonic or processing characteristics of the products or serve as pharmaceutical or additional nutritional components when used in a targeted population. Many such optional ingredients are known or otherwise suitable for use in other nutritional products and may also be used in the nutritional compositions described herein, provided that such optional ingredients are safe and effective for oral administration and are compatible with the essential and other ingredients in the composition.

Non-limiting examples of such other optional ingredients include preservatives, anti-oxidants, buffers, pharmaceutical actives, sweeteners, colorants, prebiotics, flavors, pH adjusters, citric acid, flavor enhancers, thickening agents and stabilizers, emulsifying agents, lubricants, and combinations thereof.

The nutritional compositions may further include one or more minerals, non-limiting examples of which include phosphorus, sodium, chloride, magnesium, manganese, iron, copper, zinc, iodine, calcium, potassium, chromium, molybdenum, selenium, and combinations thereof.

The nutritional compositions may also include one or more vitamins, non-limiting examples of which include carotenoids (e.g., beta-carotene, zeaxanthin, lutein, lycopene), biotin, choline, inositol, folic acid, pantothenic acid, choline, vitamin A, thiamine (vitamin B1), riboflavin (vitamin B2), niacin (vitamin B3), pyridoxine (vitamin B6), cyanocobalamin (vitamin B12), ascorbic acid (vitamin C), vitamin D, vitamin E, vitamin K, and various salts, esters, or other derivatives thereof, and combinations thereof.

In one specific embodiment of the present disclosure, the nutritional composition includes L-Glutamine, L-Arginine, calcium HMB, citric acid, a flavor, aspartame, medium chain triglycerides, acesulfame K, and artificial color.

Methods of Manufacture

The nutritional compositions may be prepared by any known or otherwise effective manufacturing technique for preparing the selected product form. Many such techniques are known for any given product form such as nutritional liquids and nutritional powders and can easily be applied by one of ordinary skill in the nutrition and formulation arts to the nutritional products described herein.

Liquid, milk or soy-based nutritional liquids, for example, may be prepared by first forming an oil and fiber blend containing all formulation oils, any emulsifier, fiber and fat-soluble vitamins. Additional slurries (typically a carbohydrate and two protein slurries) are prepared separately by mixing the carbohydrate and minerals together and the protein in water. In one embodiment, the HMB and amino acids are added into the carbohydrate slurry. The slurries are then mixed together with the oil blend. The resulting mixture is homogenized, heat processed, standardized with any water-soluble vitamins, flavored and the liquid terminally sterilized or aseptically filled or dried to produce a powder. Other manufacturing techniques, including dryblending and drymixing may also be utilized to form a powdered nutritional composition including the HMB, glutamine, and arginine.

The compositions of the present disclosure may also be manufactured by other known or otherwise suitable techniques not specifically described herein without departing from the spirit and scope of the present disclosure. The present embodiments are, therefore, to be considered in all respects as illustrative and not restrictive and that all changes and equivalents also come within the description of the present disclosure.

EXAMPLES

The following examples illustrate specific embodiments and/or features of the nutritional products of the present disclosure. The examples are given solely for the purpose of illustration and are not to be construed as limitations of the present disclosure, as many variations thereof are possible without departing from the spirit and scope of the disclosure.

The exemplified nutritional composition is prepared in accordance with manufacturing methods well known in the nutrition industry for preparing nutritional emulsions and powders.

Exemplary patent claims relating to the above-disclosed subject matter include the following. 1. A method of promoting the healing of a diabetic ulcer in a diabetic individual having a serum albumin level of less than or equal to 4 g/dL, the method comprising administering to the individual a nutritional composition comprising beta-hydroxy-beta-methylbutyrate, arginine, and glutamine. 2. The method of claim 1 wherein the diabetic ulcer is a diabetic foot ulcer. 3. The method of claim 1 wherein the nutritional composition provides the individual with from about 5 to about 20 grams per day of arginine, from about 5 to about 20 grams per day of glutamine, and from about 1 to about 10 grams per day of beta-hydroxy-beta-methylbutyrate. 4. The method of claim 1 wherein the nutritional composition provides the individual with from about 10 to about 15 grams per day of arginine, from about 10 to about 15 grams per day of glutamine, and from about 2 to about 5 grams per day of beta-hydroxy-beta-methylbutyrate. 5. The method of claim 1 wherein the nutritional composition provides the individual with about 14 grams per day of arginine, about 14 grams per day of glutamine, and about 2.4 grams per day of beta-hydroxy-beta-methylbutyrate. 6. The method of claim 1 wherein the nutritional composition comprises from about 10% to about 40% by weight arginine, from about 10% to about 40% by weight glutamine, and from about 1% to about 10% by weight calcium beta-hydroxy-beta-methylbutyrate. 7. The method of claim 1 wherein the nutritional composition comprises from about 20% to about 35% by weight arginine, from about 20% to about 35% by weight glutamine, and from about 3% to about 7% by weight calcium beta-hydroxy-beta-methylbutyrate. 8. The method of claim 1 wherein the nutritional composition comprises about 31% by weight arginine, about 32% by weight glutamine, and about 6.7% by weight calcium beta-hydroxy-beta-methylbutyrate. 9. The method of claim 1 wherein the nutritional composition further comprises at least one sweetener. 10. The method of claim 9 wherein the sweetener is sucrose. 11. The method of claim 1 wherein the nutritional composition is administered to the individual for a period of at least 6 weeks. 12. The method of claim 1 wherein the nutritional composition is administered to the individual for a period of about 16 weeks. 13. A method of promoting the healing of a diabetic ulcer in a diabetic individual having an Ankle-Brachial Index of less than 1, the method comprising administering to the individual a nutritional composition comprising beta-hydroxy-beta-methylbutyrate, arginine, and glutamine. 14. The method of claim 13 wherein the diabetic ulcer is a diabetic foot ulcer. 15. The method of claim 13 wherein the nutritional composition provides the individual with from about 5 to about 20 grams per day of arginine, from about 5.0 to about 20 grams per day of glutamine, and from about 1 to about 10 grams per day of beta-hydroxy-beta-methylbutyrate. 16. The method of claim 13 wherein the nutritional composition provides the individual with from about 10 to about 15 grams per day of arginine, from about 10 to about 15 grams per day of glutamine, and from about 2 to about 5 grams per day of beta-hydroxy-beta-methylbutyrate. 17. The method of claim 13 wherein the nutritional composition provides the individual with about 14 grams per day of arginine, about 14 grams per day of glutamine, and about 2.4 grams per day of beta-hydroxy-beta-methylbutyrate. 18. The method of claim 13 wherein the nutritional composition comprises from about 10% to about 40% by weight arginine, from about 10% to about 40% by weight glutamine, and from about 1.0% to about 10% by weight calcium beta-hydroxy-beta-methylbutyrate. 19. The method of claim 13 wherein the nutritional composition comprises from about 20% to about 35% by weight arginine, from about 20% to about 35% by weight glutamine, and from about 3% to about 7% by weight calcium beta-hydroxy-beta-methylbutyrate. 20. The method of claim 13 wherein the nutritional composition comprises about 31% by weight arginine, about 32% glutamine, and about 6.7% by weight calcium beta-hydroxy-beta-methylbutyrate. 21. The method of claim 13 wherein the nutritional composition further comprises at least one sweetener. 22. The method of claim 21 wherein the sweetener is sucrose. 23. The method of claim 13 wherein the nutritional composition is administered to the individual for a period of at least 6 weeks. 24. The method of claim 13 wherein the nutritional composition is administered to the individual for a period of about 16 weeks. 25. A method of promoting the healing of a diabetic ulcer in a diabetic individual having a serum albumin level of less than or equal to 4 g/dL and an Ankle-Brachial Index of less than 1, the method comprising administering to the individual a nutritional composition comprising beta-hydroxy-beta-methylbutyrate, arginine, and glutamine. 26. The method of claim 25 wherein the diabetic ulcer is a diabetic foot ulcer. 27. The method of claim 25 wherein the nutritional composition provides the individual with from about 5 to about 20 grams per day of arginine, from about 5 to about 20 grams per day of glutamine, and from about 1 to about 10 grams per day of beta-hydroxy-beta-methylbutyrate. 28. The method of claim 25 wherein the nutritional composition provides the individual with from about 10 to about 15 grams per day of arginine, from about 10 to about 15 grams per day of glutamine, and from about 2 to about 5 grams per day of beta-hydroxy-beta-methylbutyrate. 29. The method of claim 25 wherein the nutritional composition provides the individual with about 14 grams per day of arginine, about 14 grams per day of glutamine, and about 2.4 grams per day of beta-hydroxy-beta-methylbutyrate. 30. The method of claim 25 wherein the nutritional composition comprises from about 10% to about 40% by weight arginine, from about 10% to about 40% by weight glutamine, and from about 1.0% to about 10% by weight calcium beta-hydroxy-beta-methylbutyrate. 31. The method of claim 25 wherein the nutritional composition comprises from about 20% to about 35% by weight arginine, from about 20% to about 35% by weight glutamine, and from about 3% to about 7% by weight calcium beta-hydroxy-beta-methylbutyrate. 32. The method of claim 25 wherein the nutritional composition comprises about 31% by weight arginine, about 32% glutamine, and about 6.7% by weight calcium beta-hydroxy-beta-methylbutyrate. 33. The method of claim 25 wherein the nutritional composition further comprises at least one sweetener. 34. The method of claim 33 wherein the sweetener is sucrose. 35. The method of claim 25 wherein the nutritional composition is administered to the individual for a period of at least 6 weeks. 36. The method of claim 25 wherein the nutritional composition is administered to the individual for a period of about 16 weeks. 37. A method of promoting the healing of a diabetic ulcer in a malnourished diabetic individual, the method comprising administering to the malnourished diabetic individual a nutritional composition comprising beta-hydroxy-beta-methylbutyrate, arginine, and glutamine. 38. The method of claim 37 wherein the diabetic individual has a serum albumin level of less than or equal to 4 g/dL. 39. A method of promoting the healing of a diabetic ulcer in a diabetic individual having a reduced blood flow to the lower extremities, the method comprising administering to the individual a nutritional composition comprising beta-hydroxy-beta-methylbutyrate, arginine, and glutamine. 40. The method of claim 39 wherein the diabetic individual has an Ankle-Brachial Index of less than 1. 41. A method of promoting the healing of a diabetic ulcer in a malnourished diabetic individual having a reduced blood flow to the lower extremities, the method comprising administering to the individual a nutritional composition comprising beta-hydroxy-beta-methylbutyrate, arginine, and glutamine. 42. The method of claim 41 wherein the diabetic individual has a serum albumin level of less than or equal to 4 g/dL and an Ankle-Brachial Index of less than 1.

Example 1

In this Example, the effect of administering a nutritional composition including calcium HMB, arginine, and glutamine to diabetic subjects with diabetic foot ulcers was evaluated.

A total of 270 type 1 or type 2 diabetic subjects under pharmacological treatment for glycemic control and having at least one stage 1A diabetic foot ulcer present for at least 30 days but less than 12 months were randomized to two groups. One group received a nutritional supplement ("Test Supplement") including HMB (as calcium HMB), arginine and glutamine and the other group received a calorically similar, low glycemic response control nutritional supplement ("Control Supplement") that did not include HMB, arginine, and glutamine. Each subject consumed two drink packets per day that included either the Test Supplement or the Control Supplement. The Test and Control nutritional supplements were prepared by mixing one drink packet with 8 fluid ounces of water and were orally administered two times per day to the subjects throughout the duration of the 16-week study. It was recommended to administer the nutritional supplements with a meal. The macronutrients of the HMB, glutamine, and arginine-containing Test Supplement and the Control Supplement are set forth in the Table below.

Composition of Nutritional Supplements (per drink packet)

| Nutrient | Test Supplement | Control Supplement |
|---|---|---|
| Energy, kcal | 79* | 88 |
| Amino Acids | | |
| L-Arginine, g | 7 | 0 |
| L-Glutamine, g | 7 | 0 |
| Carbohydrate, g | 7.7 | 22.01** |
| Sugars, g | 1 | 19 |
| 1.5 g Calcium HMB provides | 1.2 g HMB | 0 |

Carbohydrate and HMB contribute 23 kcal; amino acids contribute 56 kcal.

89.5% isomaltulose, 0.5% citric acid, 4% sucrose, 6% orange juice powder.

Each of the diabetic subjects taking the Test Supplement ingested 2.4 grams of HMB per day, 14 grams of glutamine per day, and 14 grams of arginine per day. Each of the diabetic subjects taking the Control Supplement did not ingest any HMB, glutamine, or arginine from the supplement.

At the end of 16 weeks, wound healing of the diabetic ulcers was evaluated by analyzing total wound closure and time to complete healing. At baseline (at the beginning of the 16 weeks, or Visit 1), there were no differences between the subjects who received the Test Supplement and those who received the Control Supplement. Further, overall, there were no differences between the subjects in wound closure (Test Supplement: 64/129 (49.6%) as compared to Control Supplement: 65/141 (46.1%)) or time to complete wound healing at week 16.

Additionally, the interaction of serum albumin and supplementation on wound healing was also investigated. In subjects with baseline serum albumin levels of ≤4.0 g/dL (n=127), there was a significantly greater proportion of subjects with total wound healing at 16 weeks in the subjects who received the Test Supplement (31/61 (50.8%)) as compared to subjects who received the Control Supplement (23/66 (34.9%)). The Test Supplement, however, had no effect on serum albumin levels across time.

These data show that the use of an oral nutritional supplement containing arginine, glutamine, and HMB is safe and significantly improves wound healing of stage 1A diabetic foot ulcers in diabetic subjects who are at risk of malnutrition, as determined by lower serum albumin levels. The effect occurred independent of any change in albumin level over time and was significant as compared to the Control Supplement.

Additionally, the interaction of Ankle-Brachial and supplementation on wound healing was also investigated. In subjects with baseline Ankle-Brachial Index levels of less than 1.0 (n=119), there was a significantly greater proportion of subjects with total wound healing at 16 weeks in the subjects who received the Test Supplement (3/58 (60%)) as compared to subjects who received the Control Supplement (24/61 (39%)). The Test Supplement, however, had no effect on Ankle-Brachial Index across time.

These data show that the use of an oral nutritional supplement containing arginine, glutamine, and HMB is safe and significantly improves wound healing of stage 1A diabetic foot ulcers in diabetic subjects who have reduced blood flow to the lower extremities as indicated by Ankle-Brachial Index. The effect occurred independent of any change in Ankle-Brachial Index over time and was significant as compared to the Control Supplement.

Further, in diabetic subjects with a baseline Ankle-Brachial Index of less than 1.0 and a serum albumin level of less than 4.0 g/dL (n=62), there was a significantly greater proportion of diabetic subjects with a total wound healing in the diabetic subjects who consumed the Test Supplement (18/30, 60%) as compared to the Control Supplement (11/32, 34.4%). This data shows that the use of an oral nutritional composition including HMB, glutamine, and arginine is safe and significantly improves wound healing of stage 1A diabetic foot ulcers in diabetic individuals who are at risk of poor limb perfusion and malnutrition, as determined by Ankle-Brachial Index and serum albumin level.

Example 2

Example 2 illustrates a powdered nutritional composition suitable for use in the present disclosure, the ingredients of which are listed in the table below. All ingredient amounts are listed as kg per 1000 kg batch of nutritional composition, unless otherwise specified. This powdered nutritional composition is suitable for reconstitution with water or another liquid and for consumption by a diabetic individual to promote the healing of diabetic ulcers, including diabetic foot ulcers.

| Ingredient (Kg) | Amount per 1000 Kg |
|---|---|
| LGlutamine | 320.0000 |
| L-Arginine | 307.3900 |
| Citric Acid | 182.1400 |
| Calcium Beta-hydroxy-beta-methylbutyrate | 67.4400 |
| Orange Juice Powder | 63.8600 |
| Sugar | 37.9062 |
| Natural Flavors | 17.0280 |
| Aspartame | 2.1290 |
| Acesulfame Potassium | 0.8514 |
| Artificial Color | 0.2554 |
| Medium Chain Triglycerides | 1.0000 |

What is claimed is:
1. A method of promoting the healing of a diabetic foot ulcer in a diabetic individual having a malnutrition risk and/or blood flow reduction of the lower extremities, the method comprising:

determining that the diabetic individual has a malnutrition risk and/or blood flow reduction of the lower extremities, wherein the malnutrition risk is presented by a serum albumin level of less than or equal to 4.0 g/dL and wherein the blood flow reduction of the lower extremities is presented by an Ankle-Brachial Index of less than 1; and administering to the diabetic individual, for a time period of 16 weeks to less than 12 months, a nutritional composition comprising beta-hydroxy-beta-methylbutyrate, arginine, and glutamine.

2. The method of claim 1, wherein the nutritional composition provides the diabetic individual with from about 5 grams to about 20 grams per day of arginine, from about 5 grams to about 20 grams per day of glutamine, and from about 1 gram to about 10 grams per day of beta-hydroxy-beta-methylbutyrate.

3. The method of claim 1, wherein the nutritional composition provides the diabetic individual with from about 10 grams to about 15 grams per day of arginine, from about 10 grams to about 15 grams per day of glutamine, and from about 2 grams to about 5 grams per day of beta-hydroxy-beta-methylbutyrate.

4. The method of claim 1, wherein the nutritional composition provides the individual with about 14 grams per day of arginine, about 14 grams per day of glutamine, and about 2.4 grams per day of beta-hydroxy-beta-methylbutyrate.

5. The method of claim 1, wherein the nutritional composition comprises from about 10% to about 40% by weight arginine, from about 10% to about 40% by weight glutamine, and from about 1% to about 10% by weight calcium beta-hydroxy-beta-methylbutyrate.

6. The method of claim 1, wherein the nutritional composition comprises from about 20% to about 35% by weight arginine, from about 20% to about 35% by weight glutamine, and from about 3% to about 7% by weight calcium beta-hydroxy-beta-methylbutyrate.

7. The method of claim 1, wherein the nutritional composition comprises about 31% by weight arginine, about 32% by weight glutamine, and about 6.7% by weight calcium beta-hydroxy-beta-methylbutyrate.

8. The method of claim 1, wherein the nutritional composition further comprises at least one sweetener.

9. The method of claim 1, wherein the diabetic individual is malnourished.

10. The method of claim 1, wherein the diabetic individual has reduced blood flow to the lower extremities.

11. A method of promoting the healing of a diabetic foot ulcer in a diabetic individual having a malnutrition risk and/or blood flow reduction of the lower extremities, the method comprising:

determining the diabetic individual has a malnutrition risk and/or blood flow reduction of the lower extremities, wherein the malnutrition risk is presented by a serum albumin level of less than or equal to 4.0 g/dL and wherein the blood flow reduction of the lower extremities is presented by an Ankle-Brachial Index of less than 1; and administering to the diabetic individual, for a time period of 16 weeks to less than 12 months, a nutritional composition comprising beta-hydroxy-beta-methylbutyrate, arginine, and glutamine;

wherein the nutritional composition is a nutritional liquid made by reconstituting a nutritional powder; and wherein the nutritional powder comprises from about 10% to about 40% by weight arginine, from about 10% to about 40% by weight glutamine, and from about 1% to about 10% by weight calcium beta-hydroxy-beta-methylbutyrate.

12. The method of claim 1, wherein the diabetic individual has a serum albumin level of less than 2 g/dL and an Ankle-Brachial Index of less than 0.6.

13. The method of claim 11, wherein the diabetic individual has a serum albumin level of less than 2 g/dL and an Ankle-Brachial Index of less than 0.6.

14. The method of claim 1, comprising determining that the diabetic individual has at least one of a serum albumin level of less than 2.0 g/dL and an Ankle-Brachial Index of less than 0.7.

15. The method of claim 1, comprising determining that the diabetic individual has a serum albumin level of less than 2.0 g/dL and an Ankle-Brachial Index of less than 0.7.

16. The method of claim 1, wherein the nutritional composition further comprises a protein, a carbohydrate, and a fat.

17. The method of claim 1, wherein the nutritional composition further comprises a protein concentration from 8% to 32%, a carbohydrate concentration from 10% to 30%, and a fat concentration from 0.75% to 20%.

18. The method of claim 1, wherein the diabetic individual has a serum albumin level of less than or equal to 4 g/dL and an Ankle-Brachial Index of less than 1.

19. The method of claim 11, wherein the diabetic individual has a serum albumin level of less than or equal to 4 g/dL and an Ankle-Brachial Index of less than 1.

20. A method of promoting the healing of a diabetic foot ulcer in a diabetic individual having a malnutrition risk and/or blood flow reduction of the lower extremities, the method comprising:

determining the diabetic individual has a malnutrition risk and/or blood flow reduction of the lower extremities, wherein the malnutrition risk is presented by a serum albumin level of less than or equal to 4.0 g/dL and wherein the blood flow reduction of the lower extremities is presented by an Ankle-Brachial Index of less than 1; and administering to the diabetic individual, until the diabetic ulcer is closed, for a time period of 16 weeks to less than 12 months, a nutritional composition comprising beta-hydroxy-beta-methylbutyrate, arginine, and glutamine;

wherein:

the nutritional composition is a nutritional liquid made by reconstituting a nutritional powder;

the nutritional powder comprises from about 10% to about 40% by weight arginine, from about 10% to about 40% by weight glutamine, and from about 1% to about 10% by weight calcium beta-hydroxy-beta-methylbutyrate;

the nutritional composition comprises a protein concentration from 8% to 32%, a carbohydrate concentration from 10% to 30%, and a fat concentration from 0.75% to 20%;

the diabetic individual has had the diabetic ulcer for at least 30 days but less than 12 months; and the administration of the composition to the diabetic individual has no effect on the serum albumin level and no effect on the Ankle-Brachial Index of the diabetic individual over the administration time.

* * * * *